United States Patent [19]
Becker et al.

[11] Patent Number: 5,919,902
[45] Date of Patent: Jul. 6, 1999

[54] LEPTIN BOUND TO INTER-ALPHATRYPSIN INHIBITOR AND USES THEREOF

[75] Inventors: Gerald W. Becker; John E. Hale, both of Fishers, Ind.

[73] Assignee: Eli Lilly and Company, Indianapolis, Ind.

[21] Appl. No.: 08/870,864

[22] Filed: Jun. 6, 1997

Related U.S. Application Data

[60] Provisional application No. 60/019,284, Jun. 7, 1996.

[51] Int. Cl.$^6$ .......................... C07K 14/575; A61K 38/00
[52] U.S. Cl. .......................... 530/350; 530/395; 530/399; 530/402; 514/2; 514/8; 514/12
[58] Field of Search ..................... 514/2, 8, 12; 530/350, 530/399, 402, 395

[56] References Cited

U.S. PATENT DOCUMENTS

| | | |
|---|---|---|
| 5,126,249 | 6/1992 | Becker et al. |
| 5,352,769 | 10/1994 | Becker et al. |

FOREIGN PATENT DOCUMENTS

| | | |
|---|---|---|
| WO 90/08770 | 8/1990 | WIPO . |
| WO 97/26335 | 7/1997 | WIPO . |

OTHER PUBLICATIONS

Bolton and Hunter *The Biochemical Journal*, Jul. 1973, 133(3):529–539, "The Labelling of Proteins to High Specific Radioactivities by Conjugation to a $^{125}$I–Containing Acylating Agent".
Campfield, et al. *Science*, Jul. 28, 1995, 269:546–549, "Recombinant Mouse OB Protein: Evidence for a Peripheral Signal Linking Adiposity and Central Neural Networks".
Considine, et al. *The New England Journal of Medicine*, Feb. 1, 1996, 334:292–295, "Serum Immunoreactive–Leptin Concentrations in Normal–Weight and Obese Humans".
Halaas, et al. *Science*, Jul. 28, 1995, 269:543–546, "Weight–Reducing Effects of the Plasma Protein Encoded by the obese Gene".
Houseknecht, et al. *Diabetes*, Nov. 1996, 45:1638–1643, "Evidence for Leptin Binding to Proteins in Serum of Rodents and Humans: Modulation With Obesity".
Lee, et al. *Nature*, Feb. 15, 1996, 379:632–635, "Abnormal splicing of the leptin receptor in diabetic mice".
MacDougald, et al. *Proc. Natl. Acad. Sci. USA*, Sep. 1995, 92:9034–9037, "Regulated expression of the obese gene product (leptin) in white adipose tissue and 3T3–L1 adipocytes".
Maffei, et al. *Nature Medicine*, Nov. 1995, 1(11):1155–1161, "Leptin levels in human and rodent: Measurement of plasma leptin and ob RNA in obese and weight–reduced subjects".
J. Mann *Science*, Dec. 2, 1994, 266:1477–1478, "Obesity Gene Discovery May Help Solve Weighty Problem".
Miura, et al. *J. Biochem*, Feb. 1995, 117(2):400–407, "Purification and Characterization of a Novel Glycoprotein Which Has Significant Homology to Heavy Chains of Inter–α–Trypsin Inhibitor Family from Human Plasma".
NIH Consensus Conference Statement Annals Internal Medicine, Dec. 1985, 103:1073–1077, "Health Implications of Obesity".
Pelleymounter, et al. *Science*, Jul. 28, 1995, 269:540–543, "Effects of the obese Gene Product on Body Weight Regulation in ob/ob Mice".
Rink *Nature*, Dec. 1, 1994, 372:406–407, "In search of a satiety factor".
Saguchi, et al. *J. Biochem*, Jan. 1995, 117(1):14–18, "Cloning and Characterization of cDNA for Inter–α–Trypsin Inhibitor Family Heavy Chain–Releated Protein (IHRP), a Novel Human Plasma Glycoprotein".
Sinha, et al. *J. Clin. Invest.*, 1996, 97:1344–1347, "Nocturnal Rise of Leptin in Lean, Obese, and Non–Insulin–dependent Diabetes Mellitus Subjects".
Stephens, et al. *Nature*, Oct. 12, 1995, 377:530–532, "The role of neuropeptide Y in the antiobesity action of the obese gene product ".
Tartaglia, et al. *Cell*, Dec. 29, 1995, 83:1263–1271, "Identification and Expression Cloning of a Leptin Receptor, OB–R".
Zhang, et al. *Nature*, Dec. 1, 1994, 372:425–431, "Positional cloning of the mouse obese gene and its human homologue".
Considine, *Hormone Research*, 1997, 48(Suppl 5) pp. 116–121 (partial copy with only abstract provided) Bjarnason et al, European Journal Endocrinology 1997, 137, pp. 68–73 (partial copy only with abstract).
International Search Report mailed Dec. 12, 1997.
Sinha et al. Journal of Clinical Investigation, vol. 98, No. 6, Sep. 1996, 1277–1282, "Evidence of Free and Bound Leptin in Human Circulation".

*Primary Examiner*—Garnette D. Draper
*Attorney, Agent, or Firm*—Merchant & Gould

[57] ABSTRACT

A leptin binding protein, inter-alpha-trypsin inhibitor heavy chain related protein (IHRP), specifically binds leptin, the obesity gene product. The specific leptin binding proteins enable modulation of free leptin levels, immobilization and assay of bound/free leptin.

2 Claims, No Drawings

LEPTIN BOUND TO INTER-ALPHATRYPSIN INHIBITOR AND USES THEREOF

This application is a provision of Ser. No. 68/019,284 filed Jun. 7, 1996.

FIELD OF THE INVENTION

The invention relates to a binding protein for leptin, a satiety-signaling protein useful in the regulation of food intake and energy metabolism. Specifically, the serum protein inter-alpha-trypsin inhibitor family heavy chain-related protein (IHRP) has been found to specifically and with high affinity bind the Ob protein, leptin.

BACKGROUND OF THE INVENTION

Obesity is a common medical disorder which greatly increases the risk of life-threatening conditions such as high blood pressure and diabetes. The precise cause of obesity is not known, and current treatment methods have little or no success:

Recently, a gene was discovered, that, when mutated, caused severe hereditary obesity. The obesity gene (Ob gene) has been demonstrated to encode a protein, now termed leptin, which controls food intake and energy metabolism.

Leptin is primarily secreted by adipose tissue, and exerts its effects by interactions with specific receptors, e.g. in the hypothalamus. In humans, circulating leptin levels are increased in obesity and regulated by fasting, feeding, and body weight changes.

As described in the Examples below, it has now been found that the majority of circulating leptin in lean subjects with minimal adipose tissue is bound to a binding protein, whereas in obese subjects, the majority of leptin circulates as free leptin.

Modulating binding protein systems exist for circulating hormones and factors including steroid and thyroid hormones and growth factors such as insulin-like growth factor. Specific leptin binding proteins in blood could serve to modulate the active form leptin. Thus, there is a need to isolate and provide a leptin binding protein that could effectively modulate levels of bound and free leptin in circulation.

been isolated, cloned, and characterized (Zhang, et al. 1994, *Nature* 372:425–431). The Ob gene product, leptin, is an important circulating signal for the regulation of body weight. Recombinant Ob protein (leptin) purified from *E.coli*, can correct the obesity related phenotypes in ob/ob mice when exogenously administered. Weight-reducing effects of recombinant leptin were also observed in normal mice and mice with diet-induced obesity.

Leptin injected directly into the brain ventricles reduces appetite and body weight, suggesting specific brain receptors mediate leptin's effects. A leptin binding receptor, Ob-R has been isolated, cloned, and characterized. Expression of leptin receptors at high levels has been demonstrated in the hypothalamus. The putative site of leptin initiated receptor-mediated signal transduction is the hypothalamus because of its established role in energy balance, as well as the demonstration of the Ob-receptor in this tissue.

LEPTIN BINDING PROTEIN

Leptin binding proteins were isolated by screening serum proteins with a leptin affinity column, as described more fully in the Examples, below. Recombinant leptin protein was bound to a chelate resin column and incubated with serum proteins. Serum proteins that bound to the leptin column were eluted and characterized.

One specific leptin binding protein was determined to be inter-alpha-trypsin inhibitor heavy chain related protein (IHRP). The N-terminal amino acid sequence, gel electrophoresis pattern, and size (approximately 120 k Da) of the leptin binding protein purified by leptin affinity chromatography matches that of IHRP. IHRP was isolated as a leptin binding protein from both rat and human serum samples.

IHRP is a 120 k Da protein previously isolated, cloned and sequenced as a heparin-binding protein associated with plasmapheresis of patients with hypercholestereremia (LDL-apheresis). The function of IHRP is unknown.

IHRP-LEPTIN BINDING CHARACTERISTICS

IHRP has been found to bind to leptin. Specifically, a 120 K Da protein having an N-terminal sequence shown below (SEQ ID NO:1) binds specifically and with high affinity to leptin.

```
E   K   N   G   I   D   I   Y   R   L   T   V   D . . . .
Glu Lys Asn Gly Ile Asp Ile Tyr Arg Leu Thr Val Asp . . .
```

SUMMARY OF THE INVENTION

A leptin binding protein has now been isolated from serum and characterized. Specifically, inter-alpha-trypsin inhibitor heavy chain related protein(IHRP) has been isolated from serum and identified as a leptin binding protein.

As a leptin binding protein, IHRP is useful as a diagnostic and therapeutic tool, enabling purification of leptin from a sample, immobilization of leptin for assay, determination of bound versus free leptin, sequestering of therapeutic leptin for longer half-life, and/or removal of free leptin from the circulation to modulate leptin's interactions with its receptors.

DETAILED DESCRIPTION OF THE PREFERRED EMBODIMENT

LEPTIN

An obesity gene (Ob gene) has been identified that, when mutated, causes severe hereditary obesity. This gene has As used herein, the protein IHRP is meant to include the entire IHRP protein or a portion of the molecule effective in binding leptin to form a leptin-IHRP complex. One skilled in the art will recognize that the binding of leptin to IHRP will generally be due to interaction of leptin with a specific binding epitope on the IHRP molecule.

DIAGNOSTIC ASSAY FOR LEPTIN USING IHRP BINDING

The leptin binding protein, IHRP, is useful in diagnostic assays for leptin. In one embodiment, IHRP is used to immobilize leptin, e.g., to extract leptin from a mixture of proteins in a test sample or to immobilize leptin standards on an assay surface. The immobilized leptin is then further reacted, e.g., with anti-leptin antibodies to detect and/or quantitate leptin in the sample.

The leptin-IHRP complex is used to produce specific anti-complex antibodies. Such antibodies are needed for diagnostic measurement of bound versus free leptin.

In an alternative embodiment, IHRP is used to quantitate the relative amounts of bound/free leptin. For example, parallel serum samples incubated in the presence and absence of IHRP are reacted with anti-leptin antibodies. Total leptin (absence of IHRP) is reduced by the amount of free leptin (presence of IHRP) to calculate the amount of bound leptin in the sample.

THERAPEUTIC USE OF LEPTIN-IHRP COMPOSITION

As a circulating protein, an exogenously administered leptin composition is at risk of degradation, e.g. by peptidases. Binding of leptin to IHRP increases the stability of the therapeutic leptin composition in the circulation, and provides for a longer lifetime of the exogenously administered protein.

Because IHRP is a naturally-occurring leptin binding protein, administration of the bound protein mimics the normal presentation of leptin in the body, providing leptin to a site of action in a manner that can be activated and released as needed by normal body mechanisms.

THERAPEUTIC USE OF IHRP COMPOSITION

As described more fully in the Examples below, the amount of free leptin in the circulation differs in lean and obese individuals. Administration of the leptin binding protein, IHRP, to individuals with high circulating levels of leptin sequesters leptin, preventing its interaction with signal-inducing receptors.

Leptin is extremely susceptible to proteases, including trypsin, drymotrypsin and proteinase k. Binding of free leptin to binding protein reduces availability to degrading enzymes.

THERAPEUTIC AND DIAGNOSTIC KITS CONTAINING IHRP

As discussed above, IHRP-binding to leptin is a useful tool for the detection of circulating amounts of leptin, bound and free, and for the diagnosis and treatment of various food intake disorders. Diagnostic kits containing IHRP as an agent to immobilize leptin can also include specific anti-leptin antibodies. Therapeutic kits containing IHRP as a leptin binding protein can also include recombinant leptin, which can be complexed with IHRP.

Diagnostic assays for leptin are needed that can quantitate the relative amounts of bound and free leptin in the circulation. The leptin-IHRP complex is useful as an antigen for the preparation of antibodies recognizing the bound form of the leptin protein.

EXAMPLES

The invention is defined more fully below, with reference to specific examples. The data are provided as exemplary of the invention, and are not intended to limit its scope.

Example 1

Preparation of Ob Protein Affinity Column

To isolate a specific Ob protein binding protein, an affinity column containing recombinant human Ob protein was prepared. A volume of 2.5 ml of Pharmacia fast flow chelate resin (imino di-acetic acid Sepharose) was placed in each of two 10 ml syringes and rinsed with 10 ml phosphate buffered saline containing 10 mM EDTA (PBS-EDTA) and rinsed with 10 ml deionized water. The resin was loaded with 20 ml of 50 mM $CoCl_2$, rinsed with 10 ml of water, and then with 10 ml PBS (10 mM $NaPO_4$) pH7.5, 150 mM NaCl).

A Met-Arg leader was attached to the human Ob protein by the method described in U.S. Pat. Nos. 5,126,249 and 5,352,769 (MRhOb). A volume of 20 ml of MRhOb (1.5 mg/ml) was passed through the first column under gravity. PBS was run through the second column. Absorbance at 280 nm of the starting MRhOb solution was 1.27. After passing the solution through the column, the absorbance at 280 nm of the column effuluent was 0.081, indicating retention of the Ob protein on the column.

The resin from each syringe was suspended in 5 ml of PBS with 0.03% hydrogen peroxide in a 50 ml capped Falcon culture tube, and incubated at room temperature with gentle shaking for two hours. After the incubation period, the resin was poured back into the syringes, and the $H_2O_2$ buffer was decanted. The resin was rinsed with successive washes of 11 ml of PBS-EDTA, 10 ml of 0.5M imidizole in PBS, and 20 ml PBS. The absorbance at 280 nm of each wash was determined: $H_2O_2$, 0.048; PBS-EDTA, 0.07; imidizole, 0.000. The amount of Ob protein bound to the resin was estimated based on these readings to be about 27 mg Ob protein bound to about 2.5 ml resin.

Example 2

Characterization of Ob Protein Affinity Column

To characterize the region of the Ob protein bound to the resin of the affinity column described in Example 1, 200 $\mu$l of the resin slurry (about 100 $\mu$l washed resin, containing about 1 mg Ob protein) was mixed with 50 $\mu$l trypsin (1 mg/ml in PBS) and incubated at 37° C. Control MRhOb (1 mg) was similarly treated. Three samples (50 $\mu$l) of the incubating mixture were taken at one hour intervals (time 0, 1 hour, and two hours of incubation).

Peptides produced by the incubation with trypsin were separated by HPLC on a C-18 column using 25 $\mu$l of peptide solution, run with the following gradient: 0–5 minutes at 100% 0.1% trifluroacetic acid (TFA) and 5–65 minutes at 0–60% $CH_3CN$. By comparing the amino acid sequences of peptides derived from the resin with a trypsin-incubated control solution of MRhOb, differences between the resin-bound and free peptide products were noted. Nearly all of the tryptic cleavage sites in the leptin protein were accessible to cleavage by trypsin, indicating that attachment to the resin was at the N-terminus of the protein.

This study was repeated, adding a greater amount of trypsin (50 $\mu$l) to the 200 $\mu$l of Ob-resin slurry, and incubating the mixture at 37° C. overnight. The incubated resin was washed with 100% PBS, then reduced with 100 $\mu$l 0.5M EDTA and 1 $\mu$l beta-mercaptoethanol prior to HPLC on the C-18 column as described above. Results of the first study were confirmed.

Example 3

Binding of Serum Proteins to Ob Protein

Ob protein-bound resin slurry prepared as described for Example 1 (1 ml, about 5 mg Ob protein) was mixed with 1 ml of rat serum (Sigma) pre-filtered through a 0.2 $\mu$m membrane filter (Serum ACRODISC, Gellman) in a 50 ml plastic culture tube and incubated overnight (17 hours) at room temperature with gentle shaking. Control resin containing no Ob protein was similarly treated. At the end of the incubation period, the resin was poured into a 10 ml plastic column and the serum drained. The incubated resin was washed with 5 ml of 1M NaCl in PBS, 5 ml of 0.5M imidizole in PBS, and then with 3 ml of 8M UREA containing 20 mM sodium citrate, pH 6, 0.2M NaCl. One ml fractions were collected, and analyzed by polyacrylamide gel electrophoresis (PAGE).

Twenty microliters of each urea fraction was loaded per well and run in a 4–20% SDS-polyacrylamide gel. Resin samples + and − Ob protein were run in adjacent lanes of the gel. The gel was stained with Coomasie blue, and viewed for differences between the ± lanes. One particular band at about 120 k Da was present in the +Ob resin but absent in the −Ob resin.

Approximately 0.2 ml of resin (Ob+ and Ob−) was mixed with 100 μl of PAGE sample buffer (Novex) containing 5 μl Beta-mercaptoethanol. The mixture was boiled for five minutes, then 20 μl of each sample mixture was loaded onto a 4–20% SDS polyacrylamide gel. After running, the gel was electroeluted onto PVDF membrane in 10 mM CAPS (3-[cyclohexylamino]-1-propane-sulfonic acid, SIGMA), pH 11, containing 10% methanol, at 60 volts for 45 minutes. The resultant membrane was stained with Coomasie blue, and destained in 50% methanol.

A protein band of approximately 120 k daltons was noted in the Ob+ lanes and absent in the Ob− lanes. This protein was cut out of the membrane and sequenced by Edman degredation methods using an ABI 470 gas phase sequencer. The N-terminal amino acid sequence was determined to be:

```
E   K   N   G   I   D   I   Y   R   L   T   V   D . . . .     (SEQ ID NO:1).
Glu Lys Asn Gly Ile Asp Ile Tyr Arg Leu Thr Val Asp . . .
```

Example 4

IHRP is an Ob Protein Binding Protein

The GENPEPT database was searched for potential sequences matching that of the isolated Ob protein binding protein described in Example 3. One match was found: human inter-alpha-trypsin inhibitor heavy chain related protein(IHRP), a protein of approximately 120 k daltons. IHRP showed identity of 12/13 N-terminal amino acids, with $Arg^9$ of the rat protein replaced in the GENPEPT hIHRP with $Ser^9$.

Example 5

Isolation of Human IHRP by Ob Protein Binding

The binding studies described for Examples 3 and 4 were repeated using filtered human serum (binding at 37° C. for about 1 hour). The approximately 120 k dalton band was again identified in Ob+ but not Ob− lanes. This protein was excised from the Ob+ lane and sequenced as described above. A comparison of the N-terminal sequences obtained is shown below:

GENPEPT hIHRP: E K N G I D I Y S L T V D (SEQ ID NO:2)

Rat Ob-BP: E K N G I D I Y R L T V D (SEQ ID NO:1)

Human Ob-BP: E K N G ? D ? Y ? L T (SEQ ID NO:3)

Example 6

Bound and Free Leptin in Lean and Obese Individuals

Forty-six (46) individual human subjects, identified as lean or obese according to the criteria established by the National Institute of Health Consensus Development (*Ann. Intern. Med.* 1995, 103:1073–1077) and having the characteristics listed below, were studied for amounts of circulating and free leptin levels.

|  | LEAN | ObESE |
|---|---|---|
| TOTAL SUBJECTS | 46 | 30 |
| MALE | 4 | 9 |
| FEMALE | 12 | 21 |
| AGE | 30.0 ± 2.4 | 37.0 ± 2.4 |
| BODY MASS INDEX ($kg/m^2$) | 22.30 ± 0.54 | 39.1 ± 1.53 |
| PERCENT BODY FAT | 24.7 ± 1.6 | 42.0 ± 2.0 |

Percent body fat was determined by measuring bioelectric impedance (RJL Systems, Inc.) and skin-fold thickness. In six subjects, percent body fat was extrapolated from binomial equations for males and females derived from a study of 275 subjects reported in Considine et al., *New Eng. J. Med.* 1996, 334:292–5. None of the subjects had any disease except obesity, and none were in any active weight loss program or taking any drug for the treatment of obesity.

Two ml serum samples from each lean and obese individual were incubated with $^{125}$I-leptin (about 130,000 cpm, 45.6 fmoles) for 24–48 hours at 4° C., and then eluting from a Sephadex G-100 gel filtration column with 25 mM phosphate buffered saline, pH7.4, containing 0.01% sodium azide. $^{125}$I-leptin (30–42 μCi/μg) was prepared by the Bolton-Hunter method (*Biochem. J.* 1973, 133:529–39). Fifty 0.9 ml fractions were collected and $^{125}$I radioactivity was measured in a gamma counter. The gel filtration column was calibrated with blue dextran, $^{125}$I-leptin, and free $^{125}$I radioactivity.

Bound-leptin was represented by a peak of radioactivity eluting in the void volume region (peak 1), whereas free leptin was represented by a peak of radioactivity eluting in the $^{125}$I-leptin region (peak 2). After discarding the 1–3 nadir radioactive fractions, the sum of radioactivity eluted in the two peaks was calculated and the percent bound and percent free $^{125}$I-leptin was determined by dividing each by the total radioactivity eluted.

When rerun through the column, 90% of the radioactivity eluted in the first peak again eluted in the same region, suggesting no appreciable dissociation of bound $^{125}$I-leptin under the experimental conditions.

Radioactivity in peak 1, representing bound $^{125}$I-leptin complexes, was about two times higher in lean individuals (37.1±2.0% of the total radioactivity) as compared to that in obese individuals (17.8±2.9%) ($p<0.0005$). Radioactivity in peak 2, representing free leptin, was higher in obese individuals (82.16±2.91%) as compared with lean individuals (62.91±1.99%) ($p<0.0005$). These data suggest that leptin circulates bound to serum protein(s) and that the reduced peak 1 (bound leptin) observed in obese individuals is due to occupation of available binding sites by endogenous leptin.

To test this hypothesis, sera from 2 lean and 2 obese individuals was dialyzed for 72 hours at 4° C. to remove endogenous leptin (m.w. cutoff range 25,000 daltons; 25,000 mw cutoff cellulose ester tubing, Spectrum Medical Instruments, Inc.).

Using the sera depleted of endogenous leptin (with leptin concentrations of 0.3 ng/ml for lean and 3.67 ng/ml for obese), the above described experiment was repeated. Serum samples were incubated with $^{125}$I-leptin and processed through a Syphadex G-100 gel filtration column, collecting 0.9 ml fractions. In contrast to the first study, in the depleted sera differences in radioactive peaks 1 and 2 between lean and obese individuals virtually disappeared.

In obese individuals the majority of binding sites appears to be occupied by endogenous leptin. Thus, diagnostic measurement of leptin should determine the amount of circulating free leptin, to rule out the possibility that hyperleptinemia in obesity is due to an increase in bound leptin only.

Sera from 46 subjects with a wide range of body weights was fractionated and bound and free leptin was analyzed for binding to anti-leptin antibody. Serum samples (2 ml) from lean and obese individuals were fractionated by Sephadex G-100 gel filtration as described above. Approximately 25–30 fractions eluting between the void volume and the bed volume were assayed in duplicate for immunoreactive leptin using a Leptin RIA kit (Linco, Inc.). The leptin assay characteristics were the same as those described in Sinha et al., *J.Clin. Invest.* 1996, 97:1344–7. This leptin radioimmunoassay measures both bound and free leptin in serum.

Binding of leptin to serum proteins did not hinder its interaction with antibody. After calculating immunoreactive leptin eluted in peak 1 (bound from) leptin was dissociated from the binding proteins by temperature and pH changes. Reassay of the dissociated leptin gave similar amounts as the first assay of bound leptin.

Example 6

Fasting and Refeeding on Circulating Leptin Levels

The effect of short term fasting and refeeding on circulating leptin levels was studied in six female individuals, three lean and three obese.

|  | LEAN | ObESE |
|---|---|---|
| FEMALE SUBJECTS | 3 | 3 |
| AGE | 36.3 ± 3.2 | 31.0 ± 3.2 |
| BODY MASS INDEX (kg/m$^2$) | 22.7 ± 1.3 | 31.2 ± 2.3 |
| PERCENT BODY FAT | 28.3 ± 2.6 | 39.7 ± 2.3 |

During a baseline period, each individual received an isocaloric diet 30 kcal/mg/day; 50% carbohydrates, 35% fat and 15% protein) distributed among 4 meals per day. Thereafter, 24 hour fast was initiated at 9 a.m. of day 1 and then terminated at 9 a.m. of day 2. During the period of fasting, each individual received water only. During the refeeding phase which terminated at 9 a.m. of day 3, each individual received the isocaloric diet as provided during the baseline period.

Bound and free leptin levels were determined in the basal state (fasted overnight) and following 9 and 24 hour fasting (actual fasting time 20 and 36 hours, considering the 12 hour overnight fast) and 9 and 24 hours after resumption of food intake.

Table 1 summarizes bound and free circulating leptin levels in 3 lean and 3 obese females who underwent short term fasting followed by refeeding. As can be seen in Table 1, bound leptin changes little through-out the 48 hour fasting and refeeding experiment. In contrast, the changes in free leptin are rapid and significant. Particularly in lean subjects, fasting had a marked influence on free circulating leptin levels which were reduced to 0/10 of basal free leptin levels in 24 hours.

| Subjects | Basal | Fasting 9 hrs. | Fasting 24 hrs. | Refeeding 9 hrs. | Refeeding 24 hrs. |
|---|---|---|---|---|---|
| | | Free Leptin (ng/ml) | | | |
| Lean | 10.6 ± 1.9 | 4.31 ± 1.1* | 1.3 ± 0.4 | 2.7 ± 1.1* | 10.2 ± 2.6 |
| Obese | 28.3 ± 9.8 | 24.7 ± 10.3* | 14.7 ± 5.3** | 22.0 ± 8.3** | 27.1 ± 9.2 |
| | | Bound Leptin (ng/ml) | | | |
| Lean | 5.2 ± 1.0 | 3.9 ± 0.6 | 3.3 ± 0.2 | 4.1 ± 0.9 | 5.6 ± 1.1 |
| Obese | 6.3 ± 1.2 | 5.8 ± 0.5 | 5.2 ± 0.4** | 5.4 ± 0.4** | 6.2 ± 0.4 |

*P < 0.05 (against basal, paired "t" test)
**P < 0.05 (between lean and obese groups, unpaired "T" test)

It is clear, therefore, that bound and free leptin behave as different compartments in physiological alterations such as fasting and refeeding or departures from normal nutrition such as obesity. The specificity and properties of the leptin binding sites were studied. Serum from a lean individual was incubated with $^{125}$I-leptin for 72 hours at 4° C. in the absence or presence of unlabeled leptin (5–250 ng/ml) and 1 μg/ml leptin, 1 μg/ml IGF-I, or 1 μg/ml insulin, and eluted on a Sephadex G-100 column, as described above.

Bound $^{125}$I-leptin (Peak 1) in serum of a lean subject was displaced by a large excess (1 μg/ml) of unlabeled leptin. Total $^{125}$I-leptin binding in the absence of any hormone was 46.8%, whereas the non-specific binding in the presence of excess unlabeled leptin was 6.8% of the total radioactivity. The $^{125}$I-leptin binding separated by peak 1 was specific leptin binding, as insulin and IGF-I did not appreciably decrease bound-$^{125}$I-leptin eluting in peak 1.

We claim:

1. A composition comprising leptin bound to inter-alpha-trypsin inhibitor heavy chain related protein.

2. A method for extending the half-life of leptin, comprising binding leptin to inter-alpha-trypsin inhibitor heavy chain related protein.

* * * * *

UNITED STATES PATENT AND TRADEMARK OFFICE
CERTIFICATE OF CORRECTION

PATENT NO. : 5,919,902

DATED : JULY 6, 1999

INVENTOR(S) : BECKER ET AL.

It is certified that error appears in the above-identified patent and that said Letters Patent is hereby corrected as shown below:

Title page, [54] Title: "INTER-ALPHATRYPSIN" should read —INTER-ALPHA-TRYPSIN— and col. 1,.

Col. 1, line 20: "success:" should read —success.—

Col. 1, lines 46-47: move lines 46-47, which is a sequence, over to column 2, lines 46-47, under the word "leptin."

Col. 8, line 36: "4.31" should read —4.3—

Signed and Sealed this

Twenty-seventh Day of February, 2001

*Attest:*

NICHOLAS P. GODICI

*Attesting Officer*    Acting Director of the United States Patent and Trademark Office

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 13 amino acids
       (B) TYPE: amino acid
       (C) STRANDEDNESS: single
       (D) TOPOLOGY: linear (xi) SEQUENCE DESCRIPTION: SEQ ID NO:1:

Glu Lys Asn Gly Ile Asp Ile Tyr Arg Leu Thr Val Asp
   1               5                   10

(2) INFORMATION FOR SEQ ID NO:2:

(i) SEQUENCE CHARACTERISTICS:
       (A) LENGTH: 13 amino acids
       (B) TYPE: amino acid
       (C) STRANDEDNESS: single
       (D) TOPOLOGY: linear (xi) SEQUENCE DESCRIPTION: SEQ ID NO:2:

Glu Lys Asn Gly Ile Asp Ile Tyr Ser Leu Thr Val Asp
   1               5                   10

(2) INFORMATION FOR SEQ ID NO:3:

(i) SEQUENCE CHARACTERISTICS:
       (A) LENGTH: 11 amino acids
       (B) TYPE: amino acid
       (C) STRANDEDNESS: single
       (D) TOPOLOGY: linear (xi) SEQUENCE DESCRIPTION: SEQ ID NO:3:

Glu Lys Asn Gly Xaa Asp Xaa Tyr Xaa Leu Thr
   1               5                   10